US012023364B2

(12) United States Patent
Albert et al.

(10) Patent No.: US 12,023,364 B2
(45) Date of Patent: Jul. 2, 2024

(54) PROCESS FOR THE PREPARATION OF A RAW MATERIAL ENRICHED WITH ISOTHIOCYANATES AND POLYPHENOLS

(71) Applicant: SICIT GROUP SPA, Chiampo (IT)

(72) Inventors: Gretel Albert, San Lorenzo (PY); Victor Estigarribia Schinini, Lambaré (PY); Massimo Neresini, Valdagno (IT); Andres Pattini, Villarrica (PY); Chiara Pituello, Vicenza (IT); Chiara Povolo, Valdagno (IT); Alberto Rumignani, Valdagno (IT)

(73) Assignee: SICIT GROUP S.P.A., Chiampo (IT)

(*) Notice: Subject to any disclaimer, the term of this patent is extended or adjusted under 35 U.S.C. 154(b) by 361 days.

(21) Appl. No.: 17/263,373

(22) PCT Filed: Jul. 26, 2019

(86) PCT No.: PCT/EP2019/070196
§ 371 (c)(1),
(2) Date: Jan. 26, 2021

(87) PCT Pub. No.: WO2020/021071
PCT Pub. Date: Jan. 30, 2020

(65) Prior Publication Data
US 2021/0290713 A1 Sep. 23, 2021

(30) Foreign Application Priority Data

Jul. 27, 2018 (IT) .......................... 102018000007593

(51) Int. Cl.
A61K 36/185 (2006.01)
A01C 1/02 (2006.01)
A01C 1/08 (2006.01)
A01G 31/02 (2006.01)
A23L 33/105 (2016.01)

(52) U.S. Cl.
CPC .............. A61K 36/185 (2013.01); A01C 1/02 (2013.01); A01C 1/08 (2013.01); A01G 31/02 (2013.01); A23L 33/105 (2016.08); A23V 2002/00 (2013.01); A61K 2236/11 (2013.01); A61K 2236/13 (2013.01); A61K 2236/15 (2013.01); A61K 2236/51 (2013.01)

(58) Field of Classification Search
None
See application file for complete search history.

(56) References Cited

FOREIGN PATENT DOCUMENTS

| CN | 103652930 | | 3/2014 |
|---|---|---|---|
| CN | 105706875 | A | 6/2016 |
| CN | 105851942 | A | 8/2016 |
| CN | 106632534 | A | 5/2017 |
| CN | 107198226 | A | 9/2017 |
| CN | 108271601 | | 7/2018 |
| EP | 3 332 632 | | 6/2018 |
| FR | 2 834 642 | A1 | 7/2003 |
| WO | 03/057230 | | 7/2003 |

OTHER PUBLICATIONS

International Search Report for PCT/EP2019/070196, dated Sep. 6, 2019, 4 pages.
Written Opinion of the ISA for PCT/EP2019/070196, dated Sep. 6, 2019, 6 pages.
International Preliminary Report on Patentability for PCT/EP2019/070196, dated Sep. 14, 2020, 13 pages.
Office Action issued in Chinese Patent Application No. 201980049932.6 dated Dec. 22, 2022.
Crosby, "Soilless Culture of Moringa (*Moringa oleifera* Lam.) for the Production of Fresh Biomass," 2007, 137 pages.
Database WPI, Week 201861, Thomson Scientific, London, GB; AN 2018-563902, XP002787353, WPI / 2017 Clarivate Analytics, 2 pages.
Database WPI, Week 201438, Thomson Scientific, London, GB; AN 2014-J80121, XP002787354, WPI / 2017 Clarivate Analytics, 2 pages.
Tumer et al., "Direct and Indirect Antioxidant Activity of Polyphenol- and Isothiocyanate-Enriched Fractions from Moringa oleifera," Journal of Agricultural and Food Chemistry, 2015, pp. 1503-1513.
Bennett et al., "Profiling Glucosinolates and Phenolics in Vegetative and Reproductive Tissues of the Multi-Purpose Trees *Moringa oleifera* L. (Horseradish Tree) and *Moringa stenopetala* L..," Journal of Agricultural and Food Chemistry, 2003, vol. 51, pp. 3546-3553.

*Primary Examiner* — Michael V Meller
(74) *Attorney, Agent, or Firm* — NIXON & VANDERHYE

(57) ABSTRACT

Disclosed is a process for the preparation of moringa (*Moringa oleifera* Lam.) sprouts by hydroponic cultivation from seed, as well as a process for the preparation of a raw material enriched with isothiocyanates and polyphenols, starting from moringa (*Moringa oleifera* Lam.) sprouts obtained from seed by the process and/or from the adult plant, and to the raw material obtained by the process.

12 Claims, 2 Drawing Sheets

PROCESS FOR THE PREPARATION OF A RAW MATERIAL ENRICHED WITH ISOTHIOCYANATES AND POLYPHENOLS

This application is the U.S. national phase of International Application No. PCT/EP2019/070196 filed 26 Jul. 2019, which designated the U.S. and claims priority to IT Patent Application No. 102018000007593 filed 27 Jul. 2018, the entire contents of each of which are hereby incorporated by reference.

TECHNICAL FIELD OF INVENTION

The present invention relates to a process for the preparation of moringa (*Moringa oleifera* Lam.) sprouts grown from seed and to a process for the preparation of a raw material enriched with isothiocyanates (ITC) and polyphenols (PF), obtained from seed and/or from sprouts harvested from the adult plant.

PRIOR ART

It is well known that companies operating in the nutraceutical industry make a great effort to use high-quality raw materials, such quality being indicated by the type of cultivation (organic) and the active substance content.

The use of moringa in nutraceutical and cosmetic formulations has increased in recent years, almost entirely involving the use of the leaves. Moringa leaves are very interesting from the nutritional standpoint in view of their content of proteins (about 27% w/w on a dry matter basis), essential amino acids, vitamins (vitamin A, carotenoids with provitamin A potential, and vitamin C), minerals (including sodium, potassium, phosphorus, calcium and iron), and PFs with antioxidant action. ITCs and their precursors, glucosinolates, are present in the leaves, but in modest amounts compared with the other parts of the plant. The seeds are the part of the plant richest in glucosinolates, but are also the poorest in PFs.

Antioxidants can be classified as direct or indirect antioxidants, depending on their action mechanism towards free radicals. PFs, which are direct antioxidants, react directly with active radical species; conversely ITCs, as recently demonstrated (Turner et al., 2015), possess an indirect antioxidant action, ie. although they do not act directly on active radical species, they contribute to the operation of the body's defences against oxidative damage.

In general, ITCs derive from glycosylated precursors called glucosinolates, by means of a reaction mediated by the enzyme myrosinase. Glucosinolates are compounds typical of the plants belonging to the Brassicaceae family, belonging to the Capparales order, which includes *Moringa oleifera* Lam.. Also known as sulphated glycosides or thioglycosides, they are a group of glycosides consisting of a sugar part which is bonded, via a sulphur atom, to the aglycone part, derived from amino acids such as methionine, phenylalanine, tyrosine and tryptophan. As long as glucosinolates remain sequestered in the sub-cellular compartments of plant tissues, they are chemically stable and biologically inactive. Conversely, following tissue damage (caused by parasites or other factors leading to laceration of the tissues), the glycosides come into contact with myrosinase enzymes, thus activating a process of enzymatic hydrolysis of the glucosinolates, with cleavage of the β-thioglycoside linkage and formation of unstable intermediaries, and therefore with the formation of nitrogenous or sulphur-nitrogen molecules such as nitriles, thiocyanates (TC) and ITC. These products of degradation are characterised by a bitter flavour and a characteristic pungency, appreciated in dishes such as sauces and preparations based on mustard, horseradish and wasabi. Apart from their characteristic organoleptic properties which have long been known, ITCs have formed the subject of numerous studies over the years which demonstrate their anti-inflammatory, antimicrobial, anticarcinogenic and antioxidant properties.

Another method of converting glucosinolates to TC and ITC is associated with the intestinal microbiota, wherein the myrosinase specific to some micro-organisms implements the same reaction; however, the percentage of conversion to isothiocyanates is uncertain. For this reason, for health purposes, it is preferable for ITCs, which are the active molecules, to be taken directly, rather than glucosinolates.

The Scheme 1 shows the structure of the glucosinolates of *Moringa oleifera* Lam. and that of the corresponding isothiocyanates.

In particular, the main glucosinolate of moringa is 4-(α-L-rhamnopyranosiloxy)-benzyl glucosinolate (glucomoringin or GM) (compound 1 in the Scheme 1), which is present in all parts of the plant at different concentrations (Bennet et al., 2003).

Moreover, three acetyl isomers of GM (compounds 2, 3 and 4 in the Scheme 1) are present in some parts of the plant. The ITC of glucomoringin, called glucomoringin isothiocyanate (GM-ITC, compound 5 in the Scheme 1), together with the ITC of the isomer of glucomoringin acetylate in the 4' position of rhamnose (compound 8 in the Scheme 1), possess indirect antioxidant activity comparable with that of sulphoraphane, the ITC characteristic of broccoli.

Compounds 6 and 7 (Scheme 1) are the other two of the three acetylated isomers of glucomoringin.

Scheme 1

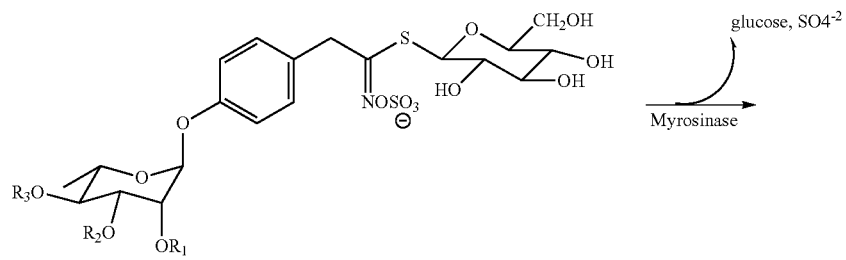

1 $R_1 = R_2 = R_3 = H$
2 $R_1 = Ac, R_2 = R_3 = H$
3 $R_2 = Ac, R_1 = R_3 = H$
4 $R_3 = Ac, R_1 = R_2 = H$

-continued

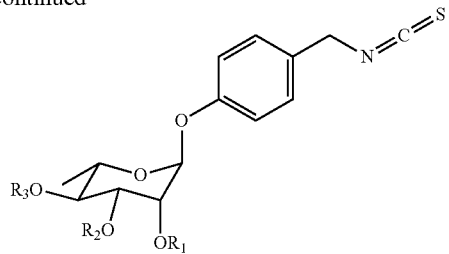

5 $R_1 = R_2 = R_3 = H$
6 $R_1 = Ac, R_2 = R_3 = H$
7 $R_2 = Ac, R_1 = R_3 = H$
8 $R_3 = Ac, R_1 = R_2 = H$

SUMMARY OF THE INVENTION

The invention relates to a process for the preparation of moringa (*Moringa oleifera* Lam.) sprouts from seed, comprising the following steps:
  a) selection of moringa seeds;
  b) preparation of seeds: optional dehusking of seeds; washing and disinfection of seeds;
  c) germination;
  d) growth under controlled soilless conditions;
  e) harvesting of aerial parts and seed and root residues.

The invention also relates to the preparation of a raw material from sprouts obtained by the process described above and/or from sprouts harvested from the adult plant of *Moringa oleifera* L., comprising the following steps:
  f) I. washing of the aerial parts of the sprouts obtained in step e) and optional disinfection of the seed and root residues obtained in step e), and/or II. washing of the aerial parts of sprouts harvested from the adult plant,
  g) extraction of the aerial parts by screw extractor to obtain a solid and a liquid,
  h) homogenisation of:
    I. the solid and liquid obtained in step g) and optionally, separately, of the seed and root residues, to obtain one or two homogeneous purées; or of:
    II. the solid and liquid obtained in step g) and the seed and root residues, combined to obtain a single homogeneous purée;
  i) removal of water from the purées obtained in step h) by drying or freeze-drying,
  j) grinding;
and it also relates to the raw material obtainable from moringa (*Moringa oleifera* L.) sprouts by said process.

DETAILED DESCRIPTION OF THE INVENTION

Figure 1:
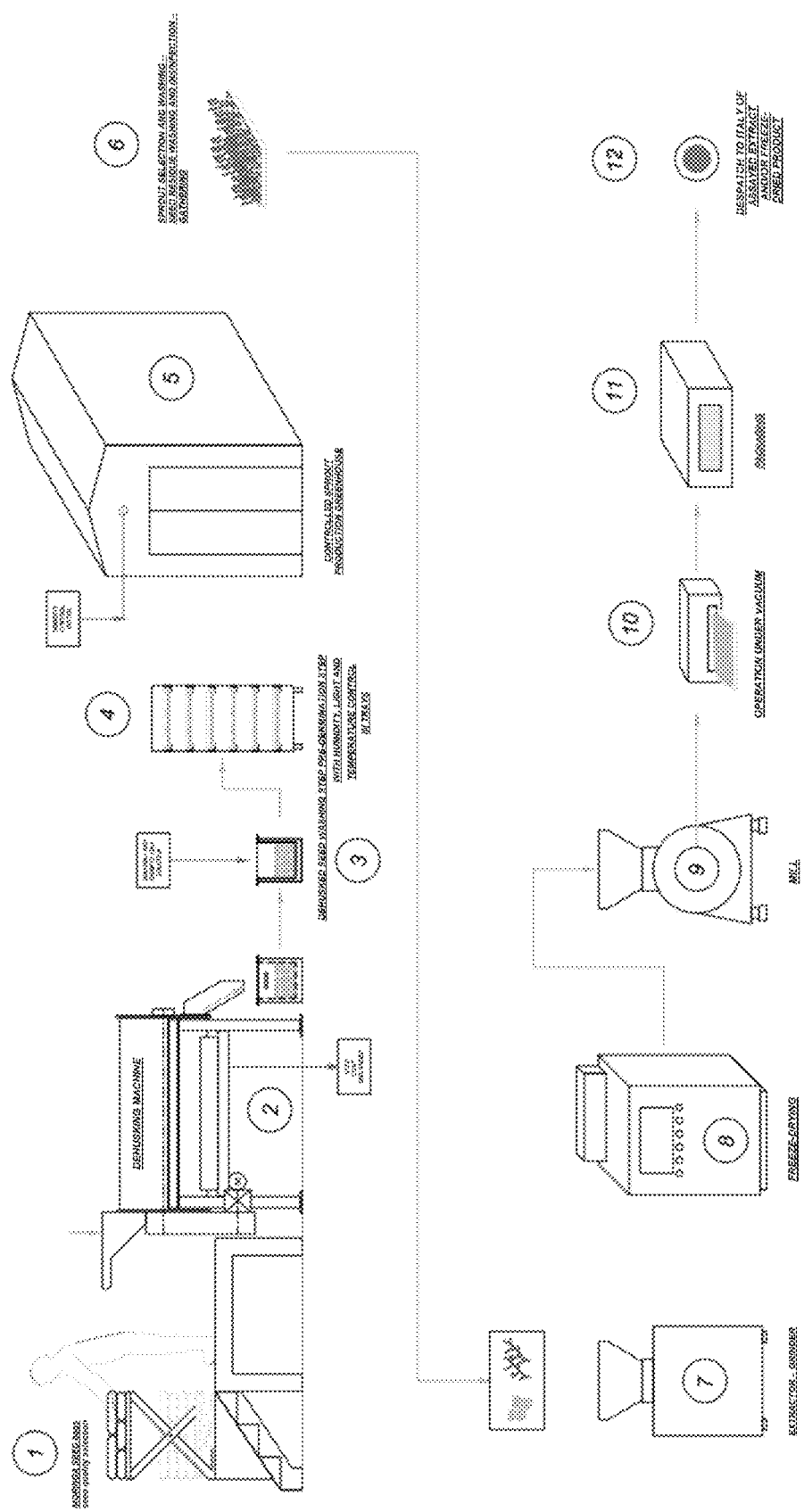
FIG. 1 shows a scheme of the process for the preparation of moringa (*Moringa oleifera* Lam.) sprouts from seed, and the raw material obtainable from said sprouts.

Object of the present invention is a process for the preparation of moringa (*Moringa oleifera* Lam.) sprouts by soilless cultivation starting from moringa seeds.

According to an embodiment of the invention, sprouts are obtained by cultivation of moringa seeds without soil and nutrient solutions.

A further object of the invention is a process for the preparation of a raw material enriched with isothiocyanates (ITC), which are known for their anti-inflammatory, antibacterial and anticarcinogenic properties, and polyphenols (PF), which are mainly known for their antioxidant action, starting from moringa (*Moringa oleifera* Lam.) sprouts grown from seed by the process according to the invention and/or from sprouts harvested from the adult plant of *Moringa oleifera* L., for example harvested directly in the field by cutting the apical part of the branches constituted by unfolding leaves and young leaves.

Sprouts prepared according to the present invention allow the production of raw materials with a high content of ITC and PF, benefiting from both the properties conferred by said classes of molecules.

Said raw materials are used in the nutraceutical and cosmetic industries, either as such or after successive extraction processes to obtain more concentrated extracts, in a form (solid or liquid) suitable for the specific field of application.

The process for the preparation of moringa (*Moringa oleifera* Lam.) sprouts from seed comprises the following steps:
  a) selection of moringa seeds;
  b) preparation of seeds: optional dehusking of seeds; washing and disinfection of seeds;
  c) germination;
  d) growth under controlled soilless conditions;
  e) harvesting of aerial parts (sprouts) and seed and root residues.

In step a), the seeds may be selected by discarding those which are broken, discoloured, mouldy or damaged.

In seed preparation step b), the seeds may optionally be dehusked, either manually or with the aid of a dehusking machine, after which the seeds may be washed by placing them, optionally dehusked, in a water bath, preferably overnight, and then rinsing them; the subsequent disinfection may be conducted by placing the seeds in a disinfectant solution, preferably an aqueous solution of calcium hydroxide or sodium hypochlorite, or an aqueous solution of glycerin macerate of citronella leaves, more preferably an aqueous solution containing from 30 to 60 g/l of calcium hydroxide or an aqueous solution containing from 0.045 to 0.55 ml/l of sodium hypochlorite or an aqueous solution containing from 100 to 300 ml/l of glycerin macerate of citronella leaves obtained by methods known from the prior art.

Disinfection preferably takes place for a time ranging from 8 to 12 hours if the disinfection is conducted with an aqueous solution of calcium hydroxide, or for a time ranging from 20 to 30 minutes if the disinfection is conducted with an aqueous solution of sodium hypochlorite or an aqueous solution of glycerin macerate of citronella leaves.

After disinfection, the seeds may be rinsed, preferably three times, to eliminate the excess disinfectant solution.

Germination then follows (step c)); the seeds may be placed in covered containers in the dark in a germinating chamber with controlled temperature and humidity for as long as necessary for full germination, preferably 3 to 5 days, to obtain the germinated seeds.

The germination temperature preferably ranges between 23° C. and 32° C., and more preferably amounts to 26° C.

The germination humidity preferably ranges between 60% and 90%, and more preferably amounts to 75%.

In step d), the germinated seeds are grown under controlled soilless conditions. For example, the germinated seeds are transferred to perforated trays and placed in a greenhouse with controlled environmental conditions (such as temperature, humidity and lighting). The temperature preferably ranges between 23° C. and 32° C., and more preferably amounts to 28° C. The sprouts are irrigated with water by sprinkling; the humidity preferably ranges between 60% and 90%, and more preferably amounts to 75%. Lighting is applied with an intensity preferably ranging between 100 and 400 $\mu mol\ m^{-2}\ s^{-1}$.

The sprouts are then harvested by making a cut above the seed, so as to separate the aerial part from the part comprising the seed and roots (step e)).

From aerial parts (sprouts) and seed and root residues thus obtained in step e), a raw material may be prepared by a process according to the invention comprising the steps described below. According to a further embodiment, the raw material may be prepared from sprouts harvested from the adult plant of *Moringa oleifera* L., either alone or combined with aerial parts (sprouts) grown from seed by the process according to the invention and seed and root residues.

The process for preparation of a raw material starting from the sprouts thus obtained by the process described above, optionally with the seed and root residues, and/or with sprouts harvested from the adult plant of *Moringa oleifera* L., comprises the following steps:

f) I. washing of the aerial parts of the sprouts obtained in step e) and optional disinfection of the seed and root residues obtained in step e), and/or II. washing of the aerial parts harvested from the adult plant, g) extraction of the aerial parts with a screw extractor to obtain a solid and a liquid, h) homogenisation of:
   I. the solid and liquid obtained in step g) and optionally, separately, the seed and root residues, to obtain one or two homogeneous purées; or:
   II. the solid and liquid obtained in step g) and the seed and root residues, combined to obtain a single homogeneous purée;

i) removal of water by drying or freeze-drying;

j) grinding.

In step f), the aerial parts of the sprouts, obtained from seed by the process according to the invention and/or harvested from the adult plant, are washed with water, while the seed and root residues, harvested separately, are disinfected in a disinfectant solution, preferably an aqueous solution of calcium hydroxide or sodium hypochlorite, or more preferably an aqueous solution containing from 30 to 60 g/l of calcium hydroxide or an aqueous solution containing from 0.045 to 0.55 ml/l of sodium hypochlorite. Alternatively, the disinfection may be conducted with an aqueous solution of glycerin macerate of citronella, preferably an aqueous solution containing from 100 to 300 ml/l of glycerin macerate of citronella leaves obtained by methods known from the prior art. Preferably, disinfection takes place for a time ranging from 8 to 12 hours if the disinfection is conducted with an aqueous solution of calcium hydroxide, or for a time ranging from 20 to 30 minutes if the disinfection is conducted with an aqueous solution of sodium hypochlorite or an aqueous solution of glycerin macerate of citronella leaves.

The seeds are then rinsed with water, preferably three times, to eliminate the disinfectant solution and obtain a biomass.

In step g) the aerial parts are introduced into a screw-type cold-press juice extractor (speed: between 60 and 75 rpm) to separate the solid from the liquid product.

In step h) I, the biomass undergoes a mechanical process of homogenisation. The solid product and the liquid product resulting from step g) and, separately, the seed and root residues, are homogenised to obtain two separate homogeneous purées (step h) I).

Alternatively, the solid product and the liquid product resulting from step g) and the seed and root residues are homogenised together to obtain a homogeneous purées (step h) II).

The water may be removed (step i)) from the homogeneous purée by drying at a temperature preferably ranging between 40° C. and 60° C., for example with an electric fan oven, or freeze-dried.

Finally, the dried or freeze-dried product obtained in step i) is ground, for example with a blade mill, to obtain the desired raw material (step j)).

According to one embodiment, the process for preparation of a raw material starting from the sprouts thus obtained by the process described above, optionally with seed and root residues, comprises the following steps:

f) I. washing of the aerial parts of the sprouts obtained in step e) and disinfection of the seed and root residues obtained in step e), g) extraction of the aerial parts with a screw extractor to obtain a solid and a liquid, h) homogenisation of:
   I. the solid and liquid obtained in step g) and optionally, separately, the seed and root residues, to obtain one or two homogeneous purées; or:
   II. the solid and liquid obtained in step g) and the seed and root residues, combined to obtain a single homogeneous purée;

i) removal of water by drying or freeze-drying;

j) grinding.

According to a further embodiment, the process for preparation of a raw material from sprouts harvested from the adult plant of *Moringa oleifera* L. and from sprouts obtained from seed by the process described above, optionally with seed and root residues, comprises the following steps:

f) I. washing of the aerial parts obtained from sprouts harvested from the adult plant of *Moringa oleifera* L. and from the sprouts obtained in step e), and optional disinfection of the seed and root residues obtained in step e), g) extraction of the aerial parts with a screw extractor to obtain a solid and a liquid, h) homogenisation of:
    III. the solid and liquid obtained in step g) and optionally, separately, the seed and root residues, to obtain one or two homogeneous purées; or:
    IV. the solid and liquid obtained in step g) and the seed and root residues, combined to obtain a single homogeneous purée;
i) removal of water by drying or freeze-drying;
j) grinding.

According to a further embodiment, the process for preparation of a raw material starting from sprouts harvested from the adult plant of *Moringa oleifera* L., comprises the following steps:
f) I. washing of the aerial parts obtained from sprouts harvested from the adult plant of *Moringa oleifera* L.,
g) extraction of the aerial parts with a screw extractor to obtain a solid and a liquid,
h) homogenisation of:
    I. the solid and liquid obtained in step g),
i) removal of water by drying or freeze-drying;
j) grinding.

A further object of the present invention is a raw material obtained from moringa sprouts by the process described above.

The following examples further illustrate the invention.

EXAMPLES

Example 1—Production of Two Different Freeze-Dried Products Derived from the Aerial Part and Seed and Root Residues Obtained from Non-Dehusked Seeds A visual selection of the seeds is made, discarding seeds which are broken, discoloured, mouldy or damaged (step a)).

The seeds are then soaked by being placed in a water bath for 8 hours. The seeds are then rinsed three times, and then disinfected by placing them in a disinfectant solution containing 0.45 ml/l of sodium hypochlorite for 30 minutes. After disinfection, the seeds are rinsed three times to eliminate the excess disinfectant solution (step b)).

Germination is then performed (step c)), by placing the seeds in covered containers in the dark in a germinating chamber for 5 days at a temperature of 26° C. and 80% humidity until the seeds germinate.

In step d), the germinated seeds are transferred to perforated trays measuring 45 cm×30 cm (1200 seeds per tray) and placed in a greenhouse with an average temperature of 29° C. and 80% humidity. Growth takes place for 15 days. The sprouts are then harvested by making a cut above the seed (step e)), so as to separate the aerial part from the part comprising the seed and roots. The fresh weight of the aerial part produced in each tray amounts to 1.7 times the dry weight of the seeds left to germinate, while the fresh weight of the seeds and roots remaining after the process amounts to 3.6 times the dry weight of the seeds left to germinate.

The aerial part of the sprouts is washed with water, while the seed and root residues are disinfected by placing them in a disinfectant solution containing 0.45 ml/l of sodium hypochlorite for 30 minutes (step f)), and then rinsed with water to eliminate the disinfectant solution and obtain a biomass.

The aerial part of the sprouts undergoes a mechanical extraction process (step g)) using a screw extractor, which operates at cold condition (room temperature) and at a low speed (60 rpm). The weight of the juice obtained amounts to 0.81 times the weight of the processed biomass, while the weight of the solid amounts to 0.12 times the weight of the biomass.

The solid product and the liquid product obtained from the aerial part are then combined and mixed in an immersion mixer to obtain a homogeneous purée. The same process is conducted for the seed and root residues (step h) I.).

The two purées obtained are freeze-dried separately to remove the water, in order to obtain a stable, storable mass (step i)). The freeze-dried product deriving from the aerial part amounts to 0.08 times the weight of the biomass subjected to freeze-drying, while that deriving from the seed and root residues amounts to 0.21 times the weight of the biomass subjected to freeze-drying. The freeze-dried products are removed from the freeze-dryer trays, then ground with a blade mill to obtain a powder (step j)), which is suitably packaged.

The resulting powder constitutes the raw material obtained from moringa sprouts forming the object of the present invention.

Example 2—Production of a Freeze-Dried Product Derived from the Aerial Part and Seed and Root Residues Obtained from Dehusked Seeds A visual selection of the seeds is made, discarding seeds which are broken, discoloured, mouldy or damaged (step a)).

The seeds are dehusked with a dehusking machine and then soaked by placing them in a water bath for 8 hours; the seeds are then rinsed three times, and then disinfected by placing them in a disinfectant solution containing 0.45 ml/l of sodium hypochlorite for 30 minutes. After disinfection, the seeds are rinsed three times to eliminate the excess disinfectant solution (step b)).

Germination is then performed (step c)), by placing the seeds in covered containers in the dark in a germinating chamber for 5 days at a temperature of 26° C. and 80% humidity until the seeds germinate.

In step d), the germinated seeds are transferred to perforated trays measuring 45 cm×30 cm (3000 seeds per tray) and placed in a greenhouse with an average temperature of 29° C. and 80% humidity. Growth takes place for 15 days. The sprouts are then harvested by making a cut above the seed (step e)), so as to separate the aerial part from the part comprising the seed and roots. The fresh weight of the aerial part produced in each tray amounts to 2.0 times the dry weight of the seeds left to germinate, while the fresh weight of the seeds and roots remaining after the process amounts to 3.2 times the dry weight of the seeds left to germinate.

The aerial part of the sprouts is washed with water, while the seed and root residues are disinfected by placing them in a disinfectant solution containing 0.45 ml/l of sodium hypochlorite for 30 minutes (step f)), and then rinsed with water to eliminate the disinfectant solution and obtain a biomass.

The aerial part of the sprouts undergoes a mechanical extraction process (step g)) using a screw extractor, which operates cold (room temperature) and at a low speed (60 rpm). The weight of the juice obtained amounts to 0.81 times the weight of the biomass, while the weight of the solid amounts to 0.12 times the weight of the biomass.

The solid products and liquid products obtained from the aerial part, and the seed and root residues, are then combined and mixed with an immersion mixer to obtain a homogeneous purée (step h) II.).

The purée obtained is freeze-dried to remove the water, in order to obtain a stable, storable mass (step i)). The freeze-dried product, amounting to 0.10 times the weight of the biomass subjected to freeze-drying, is removed from the freeze-dryer trays, then ground with a blade mill to obtain a powder (step j)), which is suitably packaged. The resulting powder constitutes the raw material obtained from moringa sprouts forming the object of the present invention.

Example 3—Production of Raw Materials Enriched with Isothiocyanates and Polyphenols from *Moringa oleifera* L. Sprouts Grown in a Controlled Environment

*Moringa oleifera* L. sprouts are grown in a greenhouse with controlled environmental parameters such as temperature, humidity and lighting, as reported in the detailed description above.

Figure 2:
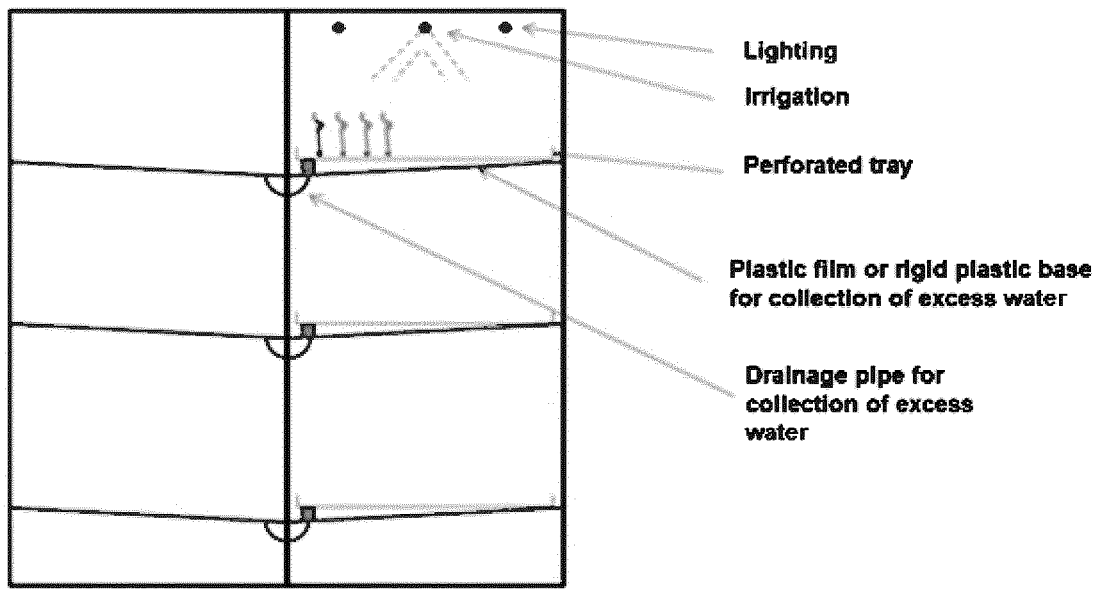
FIG. 2 shows a structure for containing the germinating trays, front view.
Figure 3:
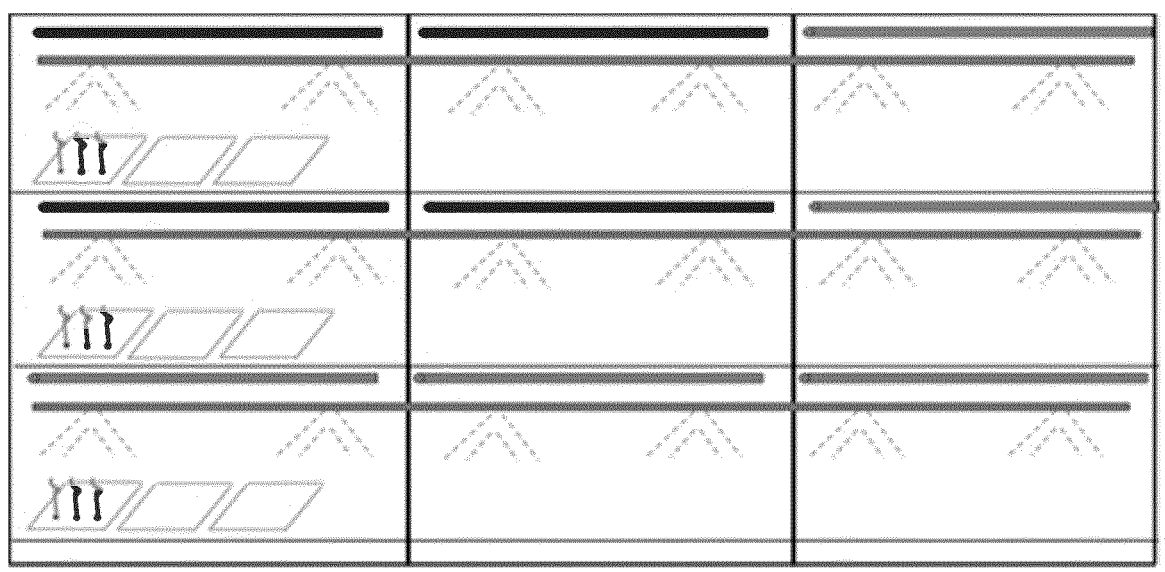
FIG. 3 shows a cross-section of the structure for containing the germinating trays, side view.

Specifically, the greenhouse has a length of 18 m, a width of 4 m and a maximum height of 4 m. Two structures in the greenhouse, which serve to contain the seed-germinating trays (FIGS. 1 and 2), have a length of 16 m, a width of 0.7 m and a height of 1.8 m, and are divided into 3 shelves, each with a height of 0.6 m. Each tray is 0.45 m long and 0.30 m wide. Each structure contains 192 trays, giving the greenhouse a total capacity of 384 trays.

The seeds are selected by discarding those which are broken, discoloured, mouldy and/or damaged. 360 g of seeds as such, previously left in a water bath overnight, rinsed, and then disinfected with an aqueous solution containing 0.45 ml/l of sodium hypochlorite for 30 minutes, are placed in each tray. Alternatively, 500 g of dehusked seeds, previously left in a water bath overnight, rinsed, and then disinfected with an aqueous solution containing 0.45 ml/l of sodium hypochlorite for 30 minutes, may be used for each tray.

The production cycle requires 5 days for seed germination and 15 days for the growth of the sprouts, making a total of 20 days, namely 16 production cycles per annum. Half the trays in the greenhouse are filled with non-dehusked seeds, and the rest with dehusked seeds. At the end of each production cycle the sprouts are harvested by making a cut above the seed, so as to separate the aerial part from the part comprising the seed and roots. The aerial part of the sprouts is washed with water, while the seed and root residues are disinfected by placing them in a disinfectant solution containing 0.45 ml/l of sodium hypochlorite for 30 minutes, and then rinsed.

1800 Kg of aerial part and 3900 Kg of seed and root residues per annum are obtained from non-dehusked seed. The aerial part of the sprouts undergoes a mechanical extraction process using a screw extractor (60 rpm) to obtain a juice and a solid residue, which are combined and mixed to obtain a homogeneous purée. The same process is conducted for the seed and root residues. The two purées obtained are then freeze-dried, with an annual output of 150 Kg of freeze-dried product from the aerial part and 800 Kg of freeze-dried product from the seed and root residues.

3000 Kg of aerial part and 4900 Kg of seed and root residues per annum are obtained from dehusked seed. The aerial part of the sprouts undergoes a mechanical extraction process using a screw extractor (60 rpm) to obtain a juice and a solid residue, which are combined and mixed with the seed and root residues to obtain a homogeneous purée. The purée is freeze-dried to obtain an annual output of 790 Kg of freeze-dried product.

BIBLIOGRAPHY

Turner, T. B., Rojas-Silva, P., Poulev, A., Raskin, I., & Waterman C. (2015). Direct and Indirect antioxidant activity of Polyphenol- and Isothiocyanate-Enriched Fractions from *Moringa oleifera*. J. Agric. Food. Chem., 63, 1505-1513.

Bennett, N. R., Mellon, F. A., Foidl, N., Pratt, J. H., Dupont, M. S., Perkins, L., & Kroon, P. A. (2003). Profiling Glucosinolates and Phenolics in Vegetative and Reproductive Tissues of the Multi-Purpose Trees *Moringa oleifera* L. (Horseradish Tree) and Moringa stenopetala L. J. Agric. Food Chem., 51, 3546-3553.

The invention claimed is:

1. A process for the preparation of moringa sprouts (*Moringa oleifera* Lam.) comprising the following steps:
   a) selection of moringa seeds;
   b) washing and disinfection of the moringa seeds;
   c) germination of the moringa seeds;
   d) growth under controlled soilless conditions;
   e) harvesting of aerial parts and the residues of seeds and roots;
   wherein the disinfection of step b) is performed by placing the seeds in a disinfectant solution selected from an aqueous solution containing from 30 g/l to 60 g/l of calcium hydroxide, an aqueous solution containing from 0.045 m/l to 0.55 ml/l of sodium hypochlorite and an aqueous solution containing from 100 ml/l to 300 ml/l of glycerin macerate of citronella leaves, for a time ranging from 8 hours to 12 hours if the disinfection is carried out with an aqueous solution of calcium hydroxide or for a time ranging from 20 minutes to 30 minutes if the disinfection is carried out with an aqueous solution of sodium hypochlorite or glycerin macerate of citronella leaves.

2. The process according to claim 1, wherein in step c) the germination temperature ranges between 23° C. and 32° C.

3. The process according to claim 1, wherein in step c) the germination humidity ranges between 60% and 90%.

4. The process according to claim 1, wherein in step d) the growth temperature ranges between 23° C. and 32° C.

5. The process according to claim 1, wherein in step d) the growth humidity ranges between 60% and 90%.

6. The process for the preparation of a raw material starting from the sprouts obtained according to the process of claim 1, comprising the following steps:
   f) washing of the aerial parts obtained in step e) and/or washing of the aerial parts harvested from the adult plant,
   g) extraction by a screw extractor of the aerial part, to obtain a solid and a liquid;
   h) homogenization of:
      the solid and liquid obtained in step g), to obtain one or two homogeneous purées; or
      the solid and liquid obtained in step g) and the seed and root residues, combined to obtain a single homogeneous purée;
   i) removing the water from the purées obtained in step h) by drying or freeze-drying; and
   j) grinding.

7. The process of claim 1, wherein the seed preparation step further comprises dehusking of the seeds.

8. The process according to claim 1, wherein in step c) the germination temperature is 26° C.

9. The process according to claim 1, wherein in step c) the germination humidity is 75%.

10. The process according to claim 1, wherein in step d) the growth temperature is 28° C.

11. The process according to claim 1, wherein in step d) the growth humidity is 75%.

12. The process of claim 6, wherein step f) further comprises disinfection of the seed and root residues obtained in step e), and wherein step h) further comprises separate homogenization of the seed and root residues.

* * * * *